United States Patent [19]

Zeikus et al.

[11] 4,403,032

[45] Sep. 6, 1983

[54] CONTINUOUS SPECTROPHOTOMETRIC ASSAY OF MICROBIAL CELLULASE

[75] Inventors: Joseph G. Zeikus, Madison, Wis.; Thomas K. Ng, Macau, Portugal

[73] Assignee: Wisconsin Alumni Research Foundation, Madison, Wis.

[21] Appl. No.: 342,352

[22] Filed: Jan. 25, 1982

Related U.S. Application Data

[63] Continuation of Ser. No. 139,281, Apr. 11, 1980, abandoned.

[51] Int. Cl.$^3$ .............................................. C12Q 1/34
[52] U.S. Cl. ...................................... 435/18; 435/29; 435/34; 435/209; 435/808
[58] Field of Search ................. 23/230 B; 435/18, 29, 435/34, 209, 808; 436/166, 171, 805

[56] References Cited

U.S. PATENT DOCUMENTS 3,676,303  7/1972  Ingelman et al. ...................... 435/18
4,066,509  1/1978  Ceska .................................... 435/18

OTHER PUBLICATIONS

Huang et al., "Sensitive Assay for Cellulase and Dextranase," *Anal. Biochem.*, 73, 1976, pp. 369–377.
*The Condensed Chemical Dictionary*, 8th Edition, 1971, pp. 85, 214, 780.
Ng et al., "A Continuous Spectro. Assay for the Deter. of Cellulase Solubilizing Activity," *Anal. Biochem.*, 103, 1980, pp. 42–50.
Ghose et al., "Measure of Cellulase Activity," IUPAC Commission on Biotechnology, Mar. 1981, pp. 1–113.

*Primary Examiner*—Peter A. Hruskoci
*Attorney, Agent, or Firm*—McDougall, Hersh & Scott

[57] ABSTRACT

A continuous spectrophotometric assay monitors the release of colored cellulose oligosaccharides during the cellulase catalyzed hydrolysis of dyed crystalline cellulose preparations. An anthraquinone derivative, Remazol Brilliant Blue R-Salt, is used to uniformly dye a variety of cellulose biopolymers without altering their respective polysaccharide conformations. The increase in dye absorbance of a cellulose filtrate is a direct measure of the total concentration of carbohydrates formed and the cellulase activity. The continuous cellulase assay has specific utility in the study of cellulase kinetics and in comparing the cellulase activities of different microorganisms.

8 Claims, 2 Drawing Figures

CONTINUOUS SPECTROPHOTOMETRIC ASSAY OF MICROBIAL CELLULASE

This is a continuation of application Ser. No. 139,281, filed Apr. 11, 1980, now abandoned.

BACKGROUND OF THE INVENTION

The most abundant cell-wall and structural polysaccharide in the plant world is cellulose, a linear polymer of D-glucose with $\beta(1-4)$ linkages. Cellulose is the principal component of wood and thus of paper; cotton is approximately 72% (by weight) pure cellulose.

On complete hydrolysis with strong acids, cellulose yields only D-glucose, but partial hydrolysis yields mainly the reducing disaccharide cellobiose, in which the linkage between the D-glucose (or anhydroglucose) units is $\beta(1-4)$, and cellulose oligosaccharides comprised of long, linear chains of anhydroglucose units.

The only chemical difference between starch and cellulose, both homopolysaccharides of D-glucose, is that starch has $\alpha(1-4)$ linkages and cellulose $\beta(1-4)$. Enzymes capable of hydrolyzing the $\beta(1-4)$ linkages of cellulose are not secreted in the digestive tract of most mammals, which therefore cannot use cellulose as food. The ruminants, however, are an exception: they can digest cellulose since bacteria in the rumen form the enzyme cellulase which hydrolyzes cellulose to D-glucose.

Cellulase is an enzyme complex comprising several components, each of which catalyzes the cleavage of a different substrate. A cellulase extract from *Trichoderma viride*, for example, contains Avicelase, carboxymethyl cellulase, cellobiase, xylanase and salicinase.

Several assay procedures have previously been used to measure the initial degradative steps in cellulose hydrolysis (also called the solubilizing activity) including: the viscosimetric method which uses carboxymethyl cellulose (CM-cellulose) as a substrate, the measurement of glucose or reducing sugars produced from native cellulose, the turbidity measurement of free fiber formation and the dinitrosalicylic acid assay to determine the concentration of reducing sugars released by CM-cellulose.

Each of these procedures, however, has one or more of the following disadvantages: substrate insensitivity, pseudosubstrate recognition, poor correlation between the actual hydrolytic products formed and the products analyzed, discontinuous measurement and interference by common end products (e.g. glucose) or sulfhydryl inhibitors.

The present invention is an improved method for the continuous spectrophotometric assay of cellulase activity in bacteria. The enzymatic degradation of a dyed crystalline cellulose is used to determine cellulase concentrations. Representative of the cellulolytic bacteria suitable for assay according to this invention are *Clostridium thermocellum* (*C. thermocellum*) and *Trichoderma viride* (*T. viride*). The continuous assay is useful in the study of cellulase kinetics and in the comparative investigation of cellulase activities in microorganisms.

Several dyed cellulose preparations can be used to measure cellulase activity. The invention, however, will hereinafter be described with respect to the use of Remazol Brilliant Blue dyed Avicel-cellulose as illustrative of the dyed cellulose substrates. Dyed-Avicel directly corresponds to the physical characteristics of native cellulose and can be easily prepared.

SUMMARY OF THE INVENTION

The release of colored cellulose oligosaccharides (total carbohydrates) during the cellulase catalyzed hydrolysis of dyed crystalline cellulose is continuously monitored. Several polysaccharides can be uniformly dyed by Remazol Brilliant Blue R-Salt (I) without an alteration in polymer conformation.

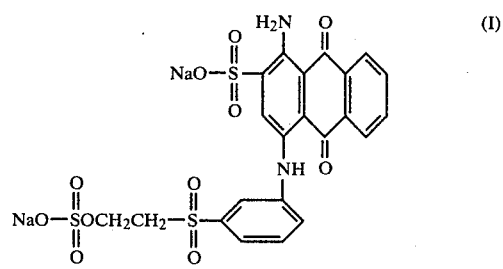

In preferred practice, however, dyed-Avicel is used as the cellulosic substrate. Avicel is a highly crystalline cellulose (62% by weight) comprised of relatively short D-glucose chains. The other possible cellulosic substrates such as Azure, CM-cellulose, trinitrophenol cellulose and phosphoric acid swollen cellulose are not crystalline, but are amorphous, and thus do not accurately represent the structure of native cellulose.

The assay is performed in a thermally controlled apparatus which continuously filters a reaction mixture of the dyed crystalline cellulose and a cellulase containing fraction. The dyed crystalline cellulose is retained on the filter, while the absorbance at 595 nm of the colored oligosaccharide containing filtrate is continuously monitored. The increase in absorbance directly correlates with the total carbohydrates formed and is a measure of cellulase activity.

DETAILED DESCRIPTION

Figure 1:
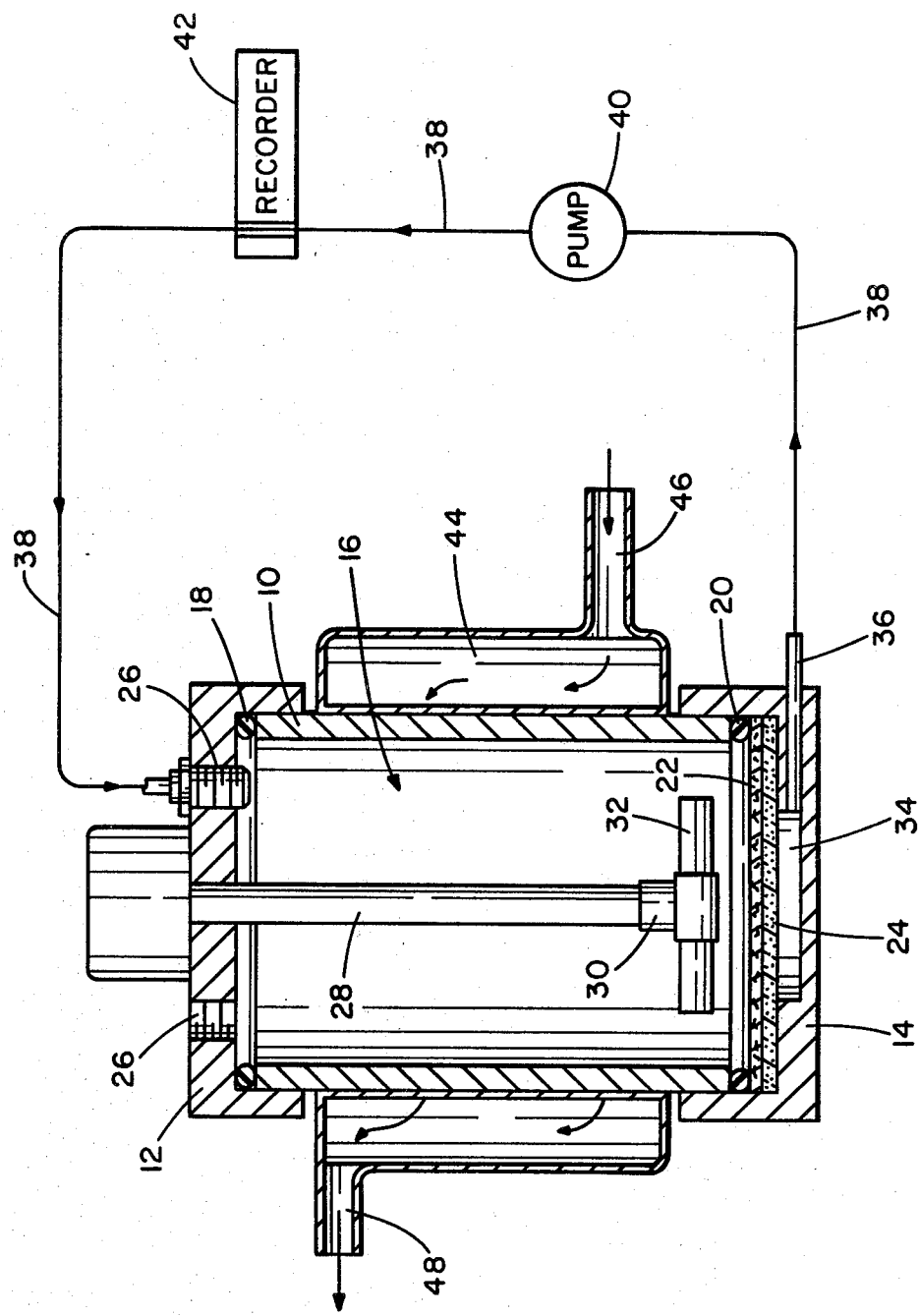
FIG. 1 is a schematic of the filtration apparatus used to perform the method of the invention.
Figure 2:
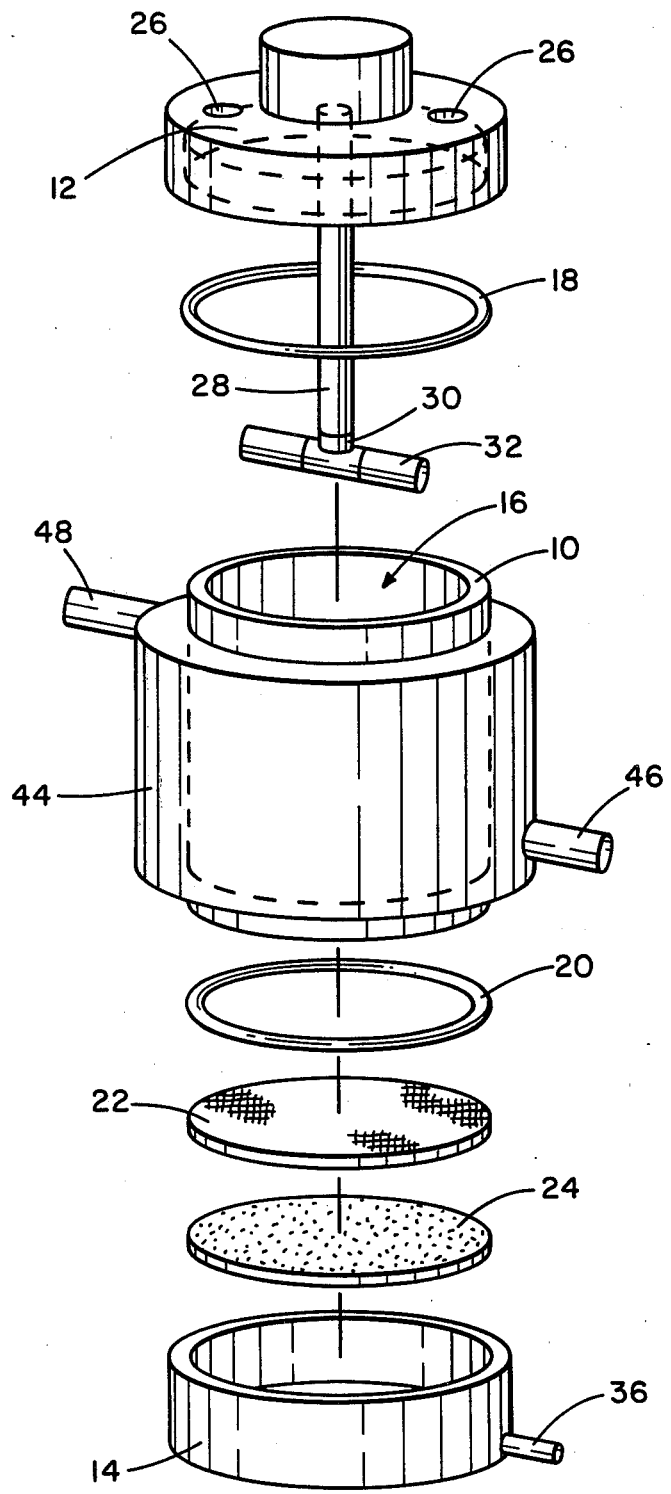
FIG. 2 is an exploded view of the filtering device of FIG. 1.

The filtration assembly of the present invention is shown in FIG. 1. The filtering device is similar to the type manufactured by the Amicon Corp. of Lexington, Mass.

A cylinder 10 is connected to a cover 12 and a base 14 to define a chamber that is thermojacketed by 44 and which is designated generally by the numeral 16. O-rings 18 and 20 provide an air and water tight seal between the cylinder 10 and both the cover 12 and the base 14, respectively. Prior to assembly, a circular filter 22 supported by a porous glass disc 24 is inserted between O-ring 20 and the base 14.

The cover 12 has at least two holes, 26 that extend through the cover to define openings through which a solution may be introduced into the chamber 16. The cover 12 also includes a center column 28 at the end of which is a rotatable member 30 adapted to receive a stirring bar 32.

The base 14 includes a channel 34 which permits the flow of filtrate from the chamber 16 to a tube 36. In communication with the tube 36 of the base 14 and also with a hole 26 of the cover 12 via flexible hose 38 are a peristaltic pump 40 and a recording spectrophotometer 42. Thus, a closed system for the flow of filtrate from the chamber 16 is provided. A suitable peristaltic pump for use in the present method is manufactured by Buchler (Fort Lee, N.J.). The absorbance of the filtrate is monitored continuously by the spectrophotometer 42 equipped with a 0.5 ml flow-through cuvette (Helma, New York, N.Y.).

A thermojacket 44 surrounds the chamber 16; water maintained at a constant temperature by a circulating thermostated bath flows through a tube 46 and the thermojacket 44 before passing through a tube 48 to recirculate. A Model FE constant temperature circulator (Haake, Saddlebrook, N.J.) was used.

The described apparatus enabled the enzyme catalyzed hydrolysis of dyed cellulose to be continuously monitored under controlled temperature and agitation conditions. The dyed products from the cleavage of cellulose by cellulase were filtered from the reaction mixture and quantified by spectrophotometric methods. The rate of hydrolysis, as measured by the increase in absorbance at 595 nm with time, was temperature dependent. As expected, the reaction rate was also dependent on the enzyme concentration.

The effect of filter pore size on the reaction rate was examined to determine the most efficient pore size for separating the dyed products from the reaction mixture and yet maintaining a rapid rate of filtration. In theory, the preferred pore size should be larger than the mean size of the products, but smaller than the dyed cellulose substrate. In this manner, the products may be readily filtered from the substrate.

Filtration rates were generally higher with larger pore size filters. Filters with a 10–20$\mu$ pore size, however, prohibited the precise measurement of absorbance due to interference from polymeric materials in the filtrate. A pore size of 5$\mu$ is preferred. In addition, nylon filters had higher filtration rates and were more durable and resistant to clogging than polycarbonate filters.

The continuous spectrophotometric assay described herein is most suitable for quantifying the rate of the initial hydrolytic reactions of crude cellulase on native crystalline cellulose. The parameter measured, absorbance change at 595 nm, correlates directly with the total carbohydrates formed. Previous methods for measuring the formation of glucose or reducing sugars are strongly dependent on the nature of the cellulase complex, such as the presence of cellobiase and the synergistic interaction between the exo- and endoglucanases. The unique aspect of cellulase solubilizing activity is the formation of long chain linear anhydroglucose units in addition to glucose and cellobiose production. This method enables the measurement of total carbohydrates released including glucose, cellobiose, and cello-oligosaccharides in the determination of the solubilizing effect of cellulase and can detect cellulase concentrations as low as 0.1 IU.

The rates of absorbance increase at 595 nm, glucose formation, reducing sugar production and total carbohydrate formation were compared during enzymatic hydrolysis of dyed-Avicel. The percentage of glucose and reducing sugars in the total amount of carbohydrate formed increased progressively during the enzymatic hydrolysis of dyed-Avicel. Thus, it appears inappropriate to measure the cellulase solubilizing activity (i.e., carbohydrate releasing activity) by assaying for glucose or reducing sugars as is common practice. On the other hand, the rate of increase of absorbance at 595 nm correlates linearly with the rate of total carbohydrate released from dyed Avicel. This validated the use of monitoring absorbance changes during the hydrolysis of dyed-Avicel to quantify the solubilizing activity of cellulase on crystalline cellulose.

The following examples illustrate the process of the present invention.

EXAMPLE 1

Preparation of the Dyed Avicel

Avicel (10 g) was suspended in 100 ml of a 50 mM sodium sulfate ($Na_2SO_4$) solution. The solution was combined with 100 ml of a 1% dye solution and stirred vigorously for 30 minutes at 60° C., while 20 g $Na_2SO_4$ was added gradually. In preferred practice, the dye used was an anthraquinone derivative, Remazol Brilliant Blue R-Salt (Reactive Blue 19). It will be understood, however, that additional Reactive dyes such as those shown in the table can be used to prepare the dyed cellulose.

TABLE I

| Commercial Name | Color Index Generic Name |
| --- | --- |
| 1. Remazol Black B | C.I. Reactive Black 5 |
| 2. Remazol Brilliant Orange RR | C.I. Reactive Orange 7 |
| 3. Remazol Brilliant Red BB | C.I. Reactive Red 21 |
| 4. Remazol Brilliant Violet 5R | C.I. Reactive Violet 5 |
| 5. Remazol Golden Yellow G | C.I. Reactive Yellow 17 |
| 6. Remazol Red B | C.I. Reactive Red 22 |
| 7. Remazol Red Violet R | C.I. Reactive Violet 4 |
| 8. Remazol Yellow GGL | C.I. Reactive Yellow 13 |
| 9. Remazol Yellow RT | C.I. Reactive Yellow 16 |

The pH of the mixture was adjusted to 12 by the addition of 5% trisodium phosphate to fix the dye to the Avicel. The mixture was then maintained at 60° C. for an additional 30 minutes, filtered through Whatman No. 1 filter paper and rinsed with 200 ml hot (55° C.) 1% sodium bicarbonate ($NaHCO_3$) solution. The dyed-Avicel was washed with hot 55° C. tap water until a clear filtrate was obtained. Washing was subsequently repeated with methanol and acetone. The powder was dried and stored under dessication at room temperature. The ether linkage between the dye and the Avicel is stable under conditions of high temperature and pH. It will also be noted that Avicel can be uniformly dyed by Remazol Brilliant Blue to 6.5% by weight without altering the physical properties of the polymer.

This dyeing procedure is not limited to Avicel and cellulose, but is applicable to other polysaccharides such as dextrans, fructans, mannans, xylans and arabinans. Each of the above polysaccharides represent a class of biopolymers designated generally by the type of monomeric repeating unit. For example, mannans are mannose homopolysaccharides found in bacteria, yeasts, molds and higher plants. Thus, the continuous spectrophotometric assay of this invention could readily be adapted for the measurement of dextranase, fructanase, mannase, xylanase and arabinase activities.

EXAMPLE 2

The procedure of example 1 was repeated using hemicellulose as the polysaccharide. Hemicellulose is not structurally related to cellulose, but is a polymer of pentoses, particularly D-xylans (polymers of D-xylose linked $\beta(1-4)$ with side chains of arabinose and other sugars). A similar stable dyed product was obtained.

EXAMPLE 3

Determination of the Degree of Polymerization ($\overline{DPn}$)

To demonstrate that the dyeing procedure did not alter the physical characteristics of a cellulose substrate, the degree of polymerization ($\overline{DPn}$) of several dyed cellulosic substrates were compared to the values of the corresponding undyed substrates.

Avicel microcrystalline cellulose (Brinkman Co., Westbury, N.Y.), Whatman cellulose CF1 and CF11 (Whatman Co., Clifton, N.J.) and Remazol Brilliant Blue R-Salt were used.

The molecular weights of the cellulosic substrates were determined from the respective methylol cellulose derivatives by high pressure gel permeation chromatography on a Stryagel column according to the following procedure.

A crystallizing dish, 170 mm in diameter, containing silicone fluid at a depth of 25 mm is placed on a stirrer-hot plate and kept at 130° C. at a level sufficient to cover two thirds of the depth of a small reaction vessel. The latter is a 15 ml capacity crystallizing dish with an outside ground glass cover. Small stirrers are prepared by inserting 12 mm lengths of iron wire into 2 mm ID glass tubing which is then sealed at the ends.

Ten mls of DMSO, 20 mg of cellulose sample and 0.3 g of paraformaldehyde powder are added to the tared dish and stirrer and the total weight recorded. The dish is then placed in the bath, a thermometer inserted, and vigorous stirring begun.

In a typical experiment, the temperature rose to 87° C. after one minute, to 105° C. at 1½ minutes and to 120° C. in two minutes. At this point, the formaldehyde began to bubble off violently. At the same time the cellulose sample quickly dissolved. Formaldehyde continued to bubble off and after two minutes the temperature was 128° C. In three minutes, bubbling had largely subsided and the clear solution was removed and placed in a hood to cool and to dispel further formaldehyde vapor. The excess formaldehyde was driven off with bone dry $N_2$ and the resulting solution passed through an HA filter (Millipore Corp.). This solution was then lyophilized at $-176°$ C. and stored dry prior to use.

Experimental

Gel permeation chromatography was performed on $10^4$ Å $\mu$-Styragel. With a flow rate of 0.5 ml dimethyl sulfoxide per minute, the back pressure developed was about 600 psi. The flow could be increased to 1.0 ml/min with a pressure of less than 1000 psi, but a slight loss of resolution was observed. Cellulose condentrations of 0.2–0.5 percent in DMSO were used with injections of 100–200 $\mu$l. A Waters model 300 chromatograph modified for micro columns and equipped with a U6K injector and was used.

Dimethyl sulfoxide (99.9 pct) was purchased from Burdick and Jackson, or was recovered as the center cut of vacuum distillation after drying over calcum hydride. Paraformaldehyde which decomposed completely at less than 135° C. was purchased from Tridom Chemical Inc. Dextran standards were purchased from Pharmacia. Methylol cellulose was prepared from wood pulps or cotton by the procedure of Nicholson and Johnson. Dextrans T500 to T10 (Pharmacia, Piscataway, N.J.) served as reference standards.

Anhydroglucose (M.W. 162) was used as the base unit in the calculation of $\overline{DPn}$. The $\overline{DPn}$ of dyed cellulose was calculated by adjusting the molecular weight of the dyed anhydroglucose monomer to equal: $162+5.14$ DS. The molecular weight of Remazol Brilliant Blue R-Salt is 514 grams per mole. The molecular weights of dyed and undyed Avicel were 76,000 and $53,000\pm10\%$, respectively.

As illustrated in the following table, the $\overline{DPn}$ values of the dyed-celluloses were similar to the undyed substrate values. In addition, the crystallinity index (CI) of each substrate was compared before and after dyeing. The crystallinity index is a number used to represent the relative state of crystallinity to cellulose as a whole. The unit is described in the October 1959 Textile Research Journal. The agreement of the CI values also indicates no alteration in the polymer structure.

TABLE II

| Substrate | $\overline{DPn}^a$ | CI[b] |
|---|---|---|
| Avicel microcrystalline | 329 | 62 |
| Dyed-Avicel | 441 | 62 |
| Whatman cellulose CF1 | 671 | 54 |
| Dyed-cellulose CF1 | 662 | 62 |
| Whatman cellulose CF11 | 547 | 56 |
| Dyed-cellulose CF11 | 615 | 61 |

[a]Degree of polymerization (anhydroglucose units).
[b]Crystallinity index (% dry weight).

EXAMPLE 4

Determination of the Degree of Substitution (DS)

The degree of substitution of a dyed cellulose substrate was calculated as follows to determine the average number of cellulose hydroxyl groups which reacted with dye.

An oven dried sample (12–24 mg) of the dyed-Avicel was dissolved with stirring for 10 minutes in 5 ml of 72% sulfuric acid at 50° C. The sample was then diluted 10–100 fold with distilled water. A 20 ml portion of the diluted sample was neutralized with 6 N sodium hydroxide and the dye concentration was spectrophotometrically determined. The dyed-Avicel showed an absorption spectrum similar to that of Remazol Brilliant Blue R-Salt after the acid hydrolysis and neutralization; the dye has an extinction coefficient ($\epsilon$) of 5901.1 $M^{-1}$ $cm^{-1}$ at 595 nm.

The degree of substitution of the dyed-Avicel sample prepared according to example 1 is 2.04 moles dye per 100 moles anhydroglucose units, with a standard deviation of 0.09.

EXAMPLE 5

The degree of substitution of a Whatman CF1 sample dyed according to the procedure of example 1 was determined as in example 4. The dyed-cellulose CF1 analyzed had a degree of substitution of 3.00 moles dye per 100 moles anhydroglucose.

The degree of substitution of a Whatman cellulose CF11 sample analyzed according to the same procedure was 2.67 moles dye per 100 moles anhydroglucose. In both analyses, the standard deviation was 0.09.

EXAMPLE 6

Continuous Assay Procedure

The described apparatus enabled the continuous monitoring of the enzymatic hydrolysis of a dyed cellulose under controlled temperature and agitation conditions. The general conditions for the continuous assay of cellulase activity in *C. thermocellum* and *T. viride* are shown in the following table with dyed-Avicel as the substrate.

TABLE III

| Conditions | C. thermocellum | T. virido |
|---|---|---|
| Total volume (ml) | 6–20 | 6–20 |
| Enzyme concentration (mg/ml) | 0.5 | 1.0 |
| Dyed-Avicel concentration (mg/ml) | 10 | 10 |
| Temperature (°C.) | 65 | 50 |
| Buffer | 0.2M sodium acetate pH 5.2 | 0.1M sodium citrate pH 4.8 |
| Time (min.) | 0–20 | 0–20 |
| Absorbance change (at 595 nm) | 0–0.5 | 0–0.5 |

As illustrated in the table, the dyed-Avicel was incubated in the chamber 16 with, for example, C. thermocellum in 6–20 ml of 0.2 M sodium acetate buffer, pH 5.2, at 65° C. The temperature was maintained constant by heated water flowing through the thermojacket 44 from a thermostated water bath. The reaction mixture was stirred at 700 rpm with a filtration rate of 50 ml per minute.

EXAMPLE 7

The relationship of the dye content in both the hydrolyzed products and the dyed-Avicel substrate was also experimentally determined. The successful use of a dyed cellulose in this assay requires that the hydrolyzed portion of the polysaccharide be uniformly dyed.

The following table shows that the amount of dye bound per anhydroglucose unit in dyed-Avicel did not significantly change during the 25 minute time course of the reaction.

TABLE IV

| Time (min) | Products Dye conc. (μg/ml) | $CHO^a$ (mg/ml) | % Dye/ CHO (w/w) | Substrate Dye conc. (mg/ml) | CHO (mg/ml) | % Dye/ CHO (w/w) |
|---|---|---|---|---|---|---|
| 0 | — | — | — | — | — | $6.8^b$ |
| 3 | 44.2 | .79 | 5.6 | 0.69 | 10.16 | 6.8 |
| 6 | 66.7 | 1.10 | 6.1 | 0.66 | 10.54 | 6.3 |
| 9 | 83.1 | 1.31 | 6.4 | 0.72 | 10.32 | 7.0 |
| 12 | 88.7 | 1.6 | 5.5 | 0.75 | 10.64 | 7.1 |
| 25 | 120.8 | 2.11 | 5.7 | 0.68 | 9.81 | 6.9 |

$^a$CHO = Total carbohydrates.
$^b$Average value.

In addition, the degree of substitution (DS) of the substrate and the products were similar when examined during the reaction. This indicates an even distribution of the dye on the degraded portion of the Avicel molecule, T. viride cellulase displayed no preference for β(1–4) bonds adjacent to either the dyed or non-dyed anhydroglucose units.

It will be understood that various changes and modifications can be made in the details of procedure, formulation and use, without departing from the spirit of the invention, especially as defined in the following claims.

We claim:

1. A method of assaying cellulase activity comprising:
    (a) contacting a dyed crystalline cellulose which represents the structure of native cellulose with either a bacterial culture or an enzyme preparation to form a medium which contains cellulase to hydrolyze the cellulose and form dyed reaction products, the portion of the cellulose that is hydrolyzed being uniformly dyed;
    (b) separating the dyed reaction products from the medium; and
    (c) determining the concentration of said dyed reaction products as a measure of the cellulose activity in said medium containing the bacterial culture or enzyme preparation whereby the concentration of dyed reaction products correlates directly with the activity of the cellulase.

2. The method according to claim 1 in which the assay is performed continuously.

3. The method according to claim 1 in which said dyed reaction products are separated from said mixture by filtering.

4. The method according to claim 1 in which the concentration of said dyed reaction products is determined spectrophotometrically.

5. The method according to claim 1 in which the bacterial culture or enzyme preparation is cellulolytic.

6. The method according to claim 1 in which said cellulase assay enables direct quantification of end product inhibitors on cellulase activity.

7. The method according to claim 1 in which the dyed crystalline cellulose is formed by contacting said crystalline cellulose with a dye in an amount sufficient to uniformly dye the crystalline cellulose under alkaline pH conditions.

8. The method according to claim 1 in which the concentration of said dyed reaction products is determined at temperatures of at least 50° C.

* * * * *